(12) United States Patent  (10) Patent No.: US 7,822,465 B2
Carls et al.  (45) Date of Patent: Oct. 26, 2010

(54) DEVICE AND METHOD FOR IMAGE-BASED DEVICE PERFORMANCE MEASUREMENT

(75) Inventors: Tommy Carls, Memphis, TN (US); Kent M. Anderson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 757 days.

(21) Appl. No.: 11/789,541

(22) Filed: Apr. 25, 2007

(65) Prior Publication Data

US 2008/0269898 A1  Oct. 30, 2008

(51) Int. Cl.
*A61B 5/05* (2006.01)
(52) U.S. Cl. .................. 600/426; 600/425; 623/17.11
(58) Field of Classification Search .......... 600/426, 600/425; 606/191, 246–261, 278, 279; 623/17.11–17.16
See application file for complete search history.

(56) References Cited

U.S. PATENT DOCUMENTS

| | | | |
|---|---|---|---|
| 5,456,724 A | 10/1995 | Yen et al. | |
| 6,706,005 B2 | 3/2004 | Roy et al. | |
| 6,723,097 B2 | 4/2004 | Fraser et al. | |
| 7,326,251 B2 * | 2/2008 | McCombe et al. | 623/17.16 |
| 2005/0245817 A1 | 11/2005 | Clayton et al. | |
| 2006/0052782 A1 | 3/2006 | Morgan et al. | |
| 2006/0106460 A1 | 5/2006 | Messerli et al. | |
| 2006/0122483 A1 | 6/2006 | Foley et al. | |
| 2006/0224088 A1 | 10/2006 | Roche | |

FOREIGN PATENT DOCUMENTS

| | | |
|---|---|---|
| WO | WO 02/055120 A2 | 7/2002 |
| WO | WO 2004/043291 A2 | 5/2004 |

* cited by examiner

*Primary Examiner*—Eduardo C Robert
*Assistant Examiner*—Christina Negrelli

(57) ABSTRACT

Devices and methods for providing in vivo performance measurements of an orthopedic implant involve an orthopedic implant having at least two radiopaque markers associated with a movable portion of the implant. The markers are positioned at known locations and in a first known and predetermined relationship to each other. The markers provide visible references upon application of a medical imaging technique to show the relative position of the markers according to a second, changed relationship to each other after implantation of the orthopedic implant. At least one measurement of performance of the implant can be determined from the first and second relationships of the markers.

24 Claims, 3 Drawing Sheets

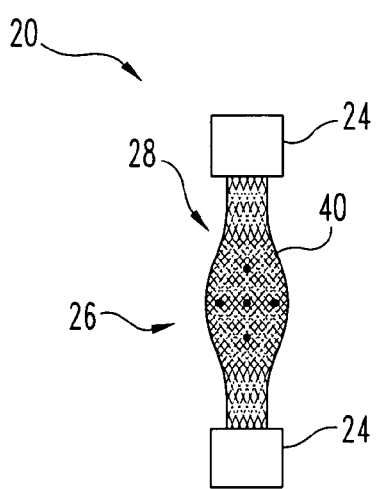
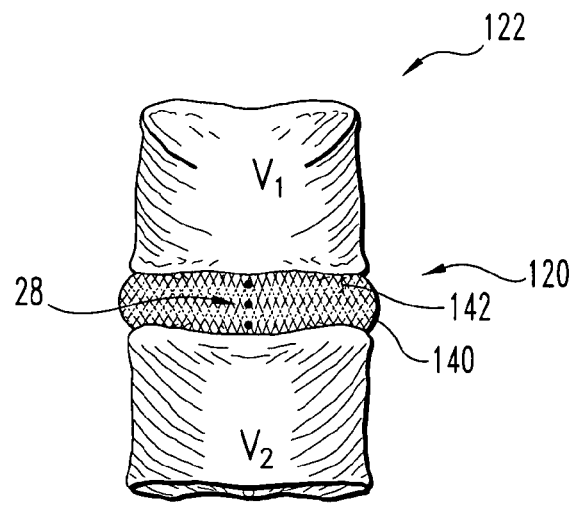
Fig. 3　　　Fig. 4
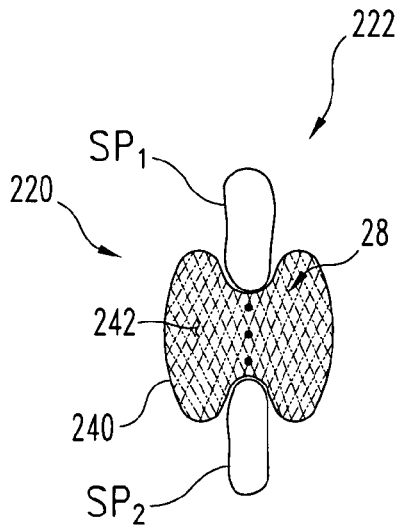
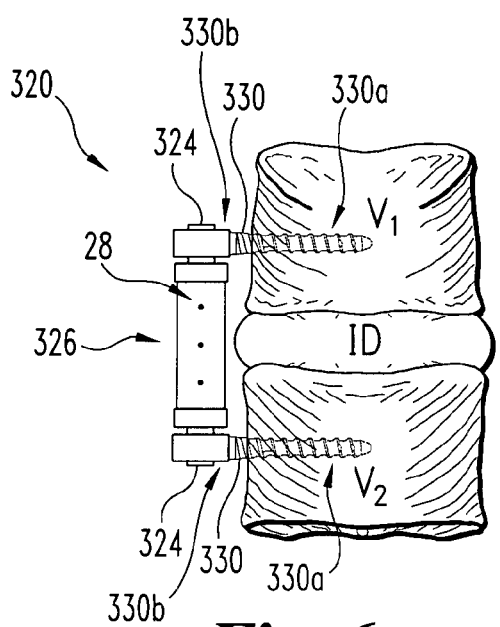
Fig. 5　　　Fig. 6

DEVICE AND METHOD FOR IMAGE-BASED DEVICE PERFORMANCE MEASUREMENT

The present disclosure broadly concerns orthopedic implant assemblies and systems useful for correction of spinal injuries or deformities. The present disclosure generally relates to devices and methods used to provide image-based, in vivo performance measurements of an orthopedic implant device or system. More specifically, but not exclusively, the present disclosure contemplates an orthopedic implant assembly having at least two radiopaque markers capable of providing visible references upon application of a medical imaging technique. Indications of performance of the orthopedic implant assembly can be determined from changes in positions and relationships of the radiopaque markers.

In the realm of orthopedic surgery, it is well known to use implants to fix the position of bones. In this way, the healing of a broken bone can be promoted, and malformations or other injuries can be corrected. For example, in the field of spinal surgery, it is well known to place such implants into or adjacent vertebrae for a number of reasons, including (a) correcting an abnormal curvature of the spine, including a scoliotic curvature, (b) to maintain appropriate spacing and provide support to broken or otherwise injured vertebrae, and (c) perform other therapies on the spinal column.

Implant and connection systems may include several pieces, which may be associated with specific other pieces. Bone screws, hooks, clamps or other fixation devices can be connected or adjoined to a particular bone as a connection between the bone and the orthopedic implant or system, which can include a support and/or stabilizing member such as a spinal rod. In such a system, a series of two or more screws may be inserted into two or more vertebrae to be instrumented. A rod, or other such appropriate implant, is then placed within or coupled to the screws, or is placed within a connecting device that links the rod and a screw, and the connections are tightened. In certain instances, screws or other such retaining members can be used to maintain the rod in a channel. In this way, a rigid supporting structure is fixed to the vertebrae, with the rod, or other such appropriate implant, providing the support that promotes correction or healing of the vertebral malformation or injury by keeping the vertebrae in a particular position.

A multitude of orthopedic implants exist for dynamic fixation of a segment of a patient's spine, positionable at various locations relative to the vertebrae of the spinal segment. In some cases, the implants incorporate flexible or movable portions or components to at least partially move in conjunction with movement of the spinal segment.

A need exists for understanding and evaluating the performance of an implanted orthopedic device in vivo.

BRIEF DESCRIPTION OF THE DRAWINGS

FIG. 3 is a front view of another embodiment of an orthopedic implant.

FIG. 4 is a front view of yet another embodiment of an orthopedic implant.

FIG. 5 is a front view of even another embodiment of an orthopedic implant.

FIG. 6 is a front view of a further embodiment of an orthopedic implant.

DESCRIPTION OF THE ILLUSTRATED EMBODIMENTS

Figure 1:
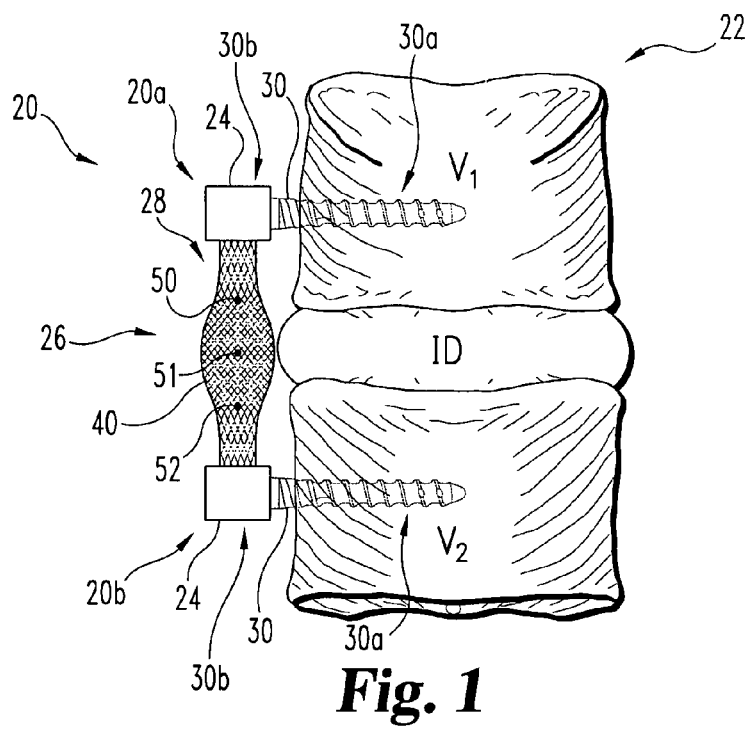
FIG. 1 is a front view of an embodiment of an orthopedic implant relative to vertebrae.

For the purposes of promoting an understanding of the principles of the disclosure, reference will now be made to the embodiment illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein, being contemplated as would normally occur to one skilled in the art to which the disclosure relates.

The present disclosure includes orthopedic devices and methods for providing image-based, in vivo performance measurement of an orthopedic implant. According to the present disclosure, embodiments of implants may include at least two radiopaque position markers associated with a flexible, movable portion of the implant. Imaging techniques can be applied to the patient to determine the relative positions of the markers and the distances therebetween, which can then be evaluated to determine various indications of performance of the implant. In response to the performance evaluation of the implant, a physician or other such medical professional can selectively alter implant properties and/or mandate certain recovery activities for the patient.

Figure 2:
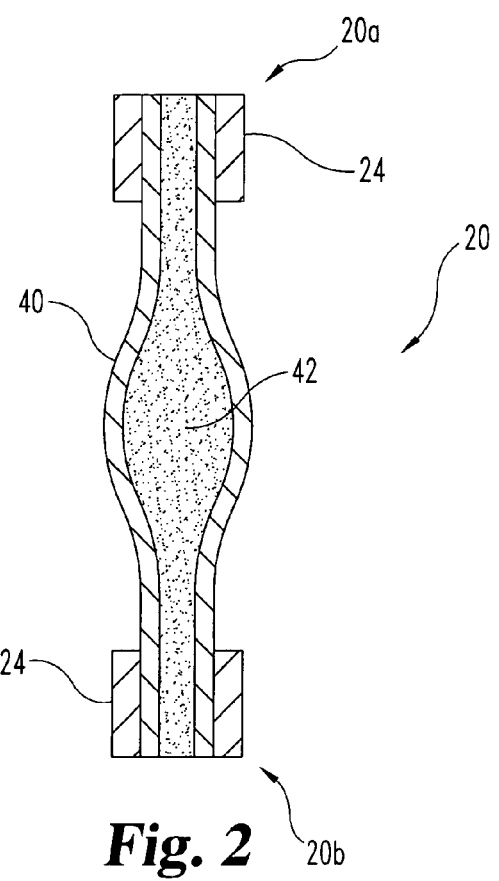
FIG. 2 is a cross-sectional view of the orthopedic implant according to the embodiment illustrated in FIG. 1.

Referring generally to FIGS. 1-3, there is shown an embodiment of an orthopedic implant assembly, including an orthopedic implant 20 secured to vertebrae via fixation elements, such as bone screws 30, which can provide correction, support or other benefit to an orthopedic surgical site. As illustrated, implant 20 can be in the form of an elongated, bulbous rod or bar to provide stability to a spinal segment 22 including vertebrae V1 and V2 and an intervertebral disc ID. Implant 20 generally includes a movable portion 26 having a set of non-powered, radiopaque markers 28 associated therewith, and can optionally include sleeves 24 at superior and inferior ends of implant 20.

Markers 28 are configured to provide a visual representation upon application of a medical imaging technique (e.g. x-ray, MRI, CT scan, or other technique) to implant 20. In certain embodiments, movable portion 26 is capable of compression, distraction, flexion, extension and/or rotation in accordance with such movements of spinal segment 22. According to the present disclosure, various measurements and other information associated with the performance of implant 20 can be determined from analysis of the relative positions of and physical relationships between markers 28.

In the illustrated embodiment, implant 20 is anchored to vertebrae V1 and V2 via fixation elements, such as bone screws 30. Bone screws 30 can include threaded bone engaging portions 30a and head portions 30b. The bone engaging portions can be at least partially advanced into a bone structure or other tissue to secure the positioning of implant 20 adjacent the underlying bone structure. In the illustrated embodiment, bone engaging portions 30a of bone screws 30 are threaded to engage vertebrae V1 and V2, and anchor implant 20 to the vertebrae. Bone engaging portions 30a of bone screws 30 can include coarse threads readily adapted for solid fixation within the cancellous bone of a vertebral body and can terminate in a tapered tip to assist in the gradual engagement and advancement of the threads into the vertebral body. Additionally, it should be appreciated that bone screws 30 can be multi-axial bone screws. However, it is contemplated that implant 20 can be anchored to the vertebrae through different means, including through the use of hooks, clamps, bolts or other such appropriate fixation members for securing implant 20 in a proper and desired position. Additionally, it is contemplated that implant 20 can be secured to vertebrae at different locations on the vertebrae than as illustrated in FIG. 1. As an example, implant 20 may be anchored to the posterior arch of the vertebrae, including the lamina.

As illustrated, sleeves 24 can optionally be positioned at superior and inferior ends 20a and 20b, respectively of implant 20. Additionally, sleeves 24 can be at least semi-permanently engaged with ends 20a and 20b as by adhesives, integral or unitary formation, or other appropriate means. In certain embodiments, sleeves 24 are composed of an appropriate metal material such as titanium for example. However it should be appreciated that sleeves 24 can be composed of other sturdy or rigid biocompatible materials. Further, sleeves 24 can be engaged with fixation elements, such as bone screws 30, by set screws, nuts, clips or other engagement members. In certain embodiments, head portions 30b of bone screws 30 can each include a receiving channel to engage the respective sleeve 24.

As illustrated in FIG. 2, an embodiment of movable portion 26 of implant 20 includes an outer jacket 40 surrounding an inner core 42. In certain embodiments, jacket 40 is composed of a compliant, yet high tensile strength, woven material. As an example, jacket 40 can be composed of a woven polyester material. However, it should be appreciated that jacket 40 can be composed of other such appropriate materials having sufficient flexibility and tensile strength. Core 42, in one embodiment, is made of a flexible, viscoelastic filler material, e.g. appropriate elastomers, such as silicone or polyurethane as examples. In the illustrated embodiment, movable portion 26 is generally bulbous in shape, at least in a middle portion. However, it should be appreciated that movable portion 26 and/or implant 20 can be shaped differently, including being generally cylindrical in shape, as an example.

Markers 28 are composed of at least one radiopaque material or substance such that markers 28 are at least somewhat impenetrable to or reflective of medical imaging radiation. It is contemplated that numerous metals or ceramics which include radiopaque properties can be used for markers 28. In certain embodiments, markers 28 are composed of barium sulfate or tantalum. In the illustrated embodiment, markers 28 are integrated into or affixed in or on woven jacket 40 of implant 20. In certain other embodiments, markers 28 can be integrated into or affixed in or on core 42 of implant 20. Additionally, it should be appreciated that markers 28 can be affixed in or to an outer surface of implant 20 (e.g. jacket 40 or core 42) as with adhesives or other appropriate means.

Markers 28 are positioned at known, predetermined positions creating a first known relationship between or among markers 28. In the embodiment illustrated in FIG. 1, there are three markers 28 aligned substantially vertically, including a superior marker 50, a medial or central marker 51 and an inferior marker 52. As another example, in the embodiment illustrated in FIG. 3 there are five markers 28 aligned substantially in a cross shape. The number and size of the radiopaque markers and the collective shape that the markers form according to the figures of the present disclosure serve as examples for illustration purposes only. It should be appreciated that the number of markers 28 associated with an orthopedic implant and the relative positioning of markers 28 can vary.

Additionally, radiopaque markers 28 assume a generally circular shape in the illustrated embodiments. However, it should be appreciated that markers 28 can include different shapes, such as square, triangular or X-shaped as examples and can be shaped differently relative to each other. Radiopaque markers 28 can be smaller or larger in size than as illustrated. Further, radiopaque markers 28 can be positioned adjacent one or more sides of the orthopedic implant, including the relative posterior, anterior and/or lateral sides. In the illustrated embodiments, markers 28 are positioned on the moveable portions of the orthopedic implants. However, it should be appreciated that markers 28 can be positioned in or on other portions of the implants as would occur to one skilled in the art, including non-moveable or relatively rigid portions such as sleeves 24. Overall, radiopaque markers 28 can be configured, positioned and arranged to a multitude of appropriate manners such that markers 28 provide a visible reference upon application of a medical imaging technique as described below.

FIG. 4 illustrates an orthopedic implant 120 according to another embodiment of the present disclosure to provide stability to a spinal segment 122. As illustrated, implant 120 is an artificial disc implant designed to at least partially replace and mimic the function of an intervertebral disc between adjacent vertebrae, such as vertebrae V1 and V2. Implant 120 includes radiopaque markers 28 associated with a movable portion 126.

Markers 28 provide a visual representation upon application of a medical imaging technique, thereby allowing for in vivo performance measurement of implant 120. It should be appreciated that markers 28 can be configured, integrated, positioned and arranged relative to implant 120 as described above in connection with implant 20 and/or according to other appropriate manners as would generally occur to one skilled in the art, such that markers 28 provide visible references upon application of a medical imaging technique. Additionally, it is contemplated that markers 28 can number more or less than three on implant 120 as would occur to one skilled in the art.

In certain embodiments, movable portion 126 is capable of compression, distraction, flexion, extension and/or rotation in accordance with such movements of spinal segment 122. Additionally in certain embodiments, movable portion 126 of implant 120 can include an outer woven jacket 140 surrounding an inner core 142, with markers 28 integrated into or affixed on or to jacket 140 or core 142. Jacket 140 and core 142 can be configured and composed of similar materials as described above in connection jacket 140 and core 142. However, it should be appreciated that implant 120 can be configured differently and markers 28 can be integrated into implant 120 in different manners as would occur to one skilled in the art.

Referring to FIG. 5, there is shown an orthopedic implant 220 according to another embodiment of the present disclosure to provide stability to a spinal segment 222. As illustrated, implant 220 is an intervertebral spacer implant positioned between adjacent spinus processes SPI and SP2 of adjacent vertebrae, with the remainder of the vertebrae not shown in FIG. 5 for the sake of clarity and brevity. Implant 220 includes radiopaque markers 28 associated with a movable portion 226 to provide a visual representation upon application of a medical imaging technique, thereby allowing for in vivo performance measurement of implant 220. It should be appreciated that markers 28 can be configured, integrated, positioned and arranged with respect to implant 220 as described above in connection with implants 20 and/or 120, and/or according to other appropriate manners. Additionally, it is contemplated that markers 28 can number more or less than three on implant 220 as would occur to one skilled in the art.

In certain embodiments, movable portion 226 is capable of compression, distraction, flexion, extension and/or rotation in accordance with such movements of spinal segment 222. In certain embodiments, movable portion 226 can include an outer woven jacket 240 surrounding an inner core 242, with markers 28 integrated into or affixed on or in jacket 240 or core 242. Jacket 240 and core 242 can be configured and composed of similar materials as described above in connection with jacket 40 and core 42. It should be appreciated that implant 220 can be configured differently and markers 28 can be integrated into implant 220 in different manners as would occur to one skilled in the art.

Referring to FIG. 6, orthopedic implant 320 is shown according to another embodiment of the present disclosure to provide stability to a spinal segment 322. As illustrated, implant 320 is positionable adjacent vertebrae V1 and V2 and intervertebral disc ID. In the illustrated embodiment, implant 320 is a generally elongated, spinal rod having end sections 324 adjacent superior and inferior ends of an intermediate movable or flexible section 326. In certain embodiments, end sections 324 are composed of an appropriate biocompatible metal material, such as stainless steel or titanium or alloys, or other rigid or sturdy material. Movable section 326 can be composed of flexible biocompatible materials such as polymeric, elastomeric or rubber materials. In certain other embodiments, movable section 326 includes an outer woven jacket surrounding an inner viscoelastic core, similar to jacket 40 and core 42 described above.

Implant 320 is anchored to vertebrae V1 and V2 via any appropriate fixation method, such as through the use of bone screws 330. In the illustrated embodiment, bone screws 330 include bone engaging portions 330a and head portions 330b configured to engage end sections 324 of implant 320 to secure the implant to the vertebrae. However, it should be appreciated that implant 320 can be anchored to the vertebrae through different structures (e.g. hooks or clamps) and at different locations on the vertebrae than as illustrated in FIG. 6.

Implant 320 includes radiopaque markers 28 associated with movable portion 326 to provide a visual representation upon application of a medical imaging technique and thereby allowing for in vivo performance measurement of implant 320. It should be appreciated that markers 28 can be configured, integrated, positioned and/or arranged relative to implant 320 as described above in connection with implants 20, 120 and/or 220, and/or according to other appropriate manners. Further, markers 28 can number more or less than three on implant 320. In certain embodiments, movable portion 326 is capable of compression, distraction, flexion, extension and/or rotation in accordance with such movements of spinal segment 322.

Generally regarding the present disclosure, it is contemplated that other appropriate orthopedic implants designed to allow for at least partial rotation and bending can be used with the systems and methods of the present disclosure, involving the use of radiopaque markers in providing in vivo performance measurements of the particular implant.

Figure 7A:
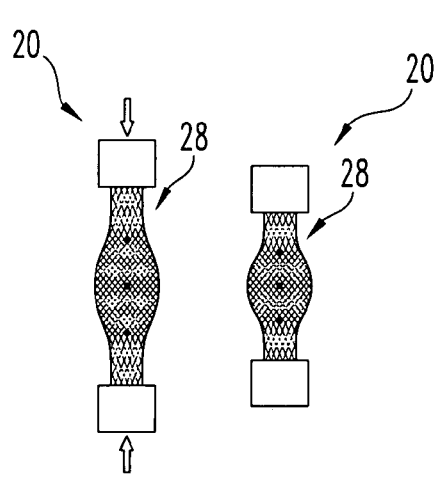
FIGS. 7A-7E are front views of an orthopedic implant according to the embodiment illustrated in FIGS. 1-3, and according to various motions.
Figure 7B:
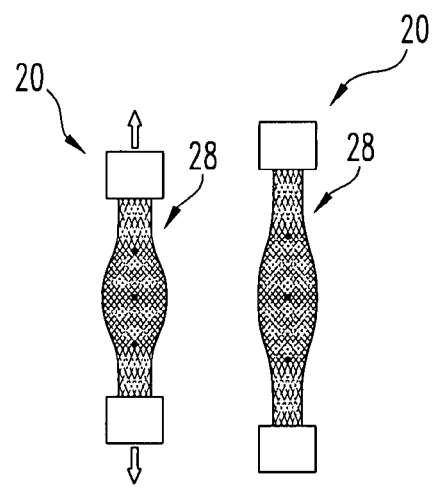
Figure 7C:
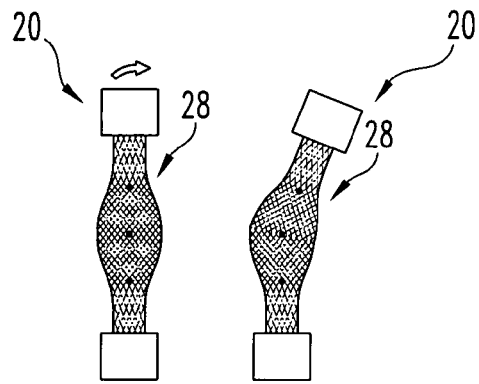
Figure 7D:
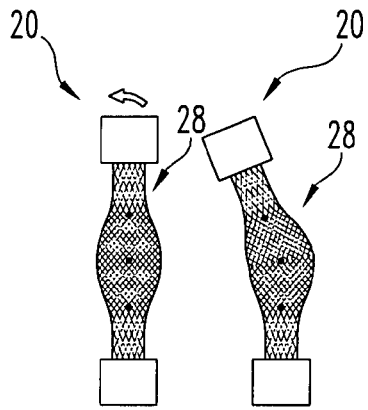
Figure 7E:
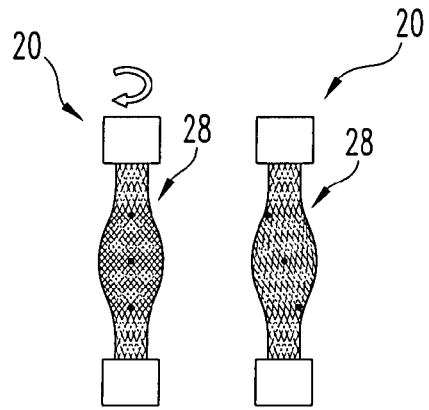

FIGS. 7A-7E illustrate implant 20 according to different motions of a spinal segment, including compression (FIG. 7A), distraction (FIG. 7B), flexion (FIG. 7C), extension (FIG. 7D) and rotation (FIG. 7E). For the purposes of the present disclosure, it is contemplated that flexion includes bending forward or toward the anterior, and extension includes bending backward or toward the dorsal or posterior. Additionally, it should be appreciated that orthopedic implant 20 is shown for illustration purposes only and other appropriate flexible orthopedic implants could be utilized, including those described above in connection with other embodiments.

Referring generally to FIGS. 7A-7E, each figure includes two illustrations of implant 20 with the left illustrations representing implant 20 in a neutral position and the right illustrations representing implant 20 according to the motions described above. The left illustrations of implant 20 show markers 28 at first positions according to a first known and predetermined relationship. As can be seen from the right illustrations, movements of implant 20 can create different physical relationships between markers 28 based on the changed relative positions thereof and the changed distances therebetween. Various indications of performance of implant 20 can be determined from the changed relative positions and relationships of markers 28, as described below.

Referring generally to FIGS. 1-7E, the operation and use of the orthopedic implants discussed and illustrated herein will be described with reference to a surgical procedure involving a section of spine. It should be appreciated that the methods described herein involve the use of one or more orthopedic implants incorporating radiopaque markers, such as implant 20, 120, 220 and/or 320. It will also be appreciated that other uses of the implants described herein and other surgical procedures can be made.

To treat the condition or injury of the patient, the surgeon obtains access to the surgical site in any appropriate manner, e.g. through incision and retraction of tissues. It is contemplated that the orthopedic implants discussed herein can be used in minimally-invasive surgical techniques where the disc space is accessed through a micro-incision, a sleeve, or one or more retractors that provide a protected passageway to the disc space. The orthopedic implants discussed herein also have application in open surgical techniques where skin and tissue are incised and retracted to expose the surgical site.

Once access to the surgical site has been obtained, e.g. via an opening such as a midline incision above the affected area, with tissue being resected, or by other surgical procedure, the surgeon may implant one or more orthopedic implants, such as orthopedic implants 20, 120, 220 and/or 320 discussed herein, adjacent vertebrae of a spinal segment that require compression or distraction in order to relieve or improve their condition. In some cases which require connection of the orthopedic implant to the adjacent vertebrae, pilot holes in vertebrae may be made, and fixation elements, such as bone screws 30 and/or 330, may be inserted into or otherwise connected to two or more vertebrae. Bone engaging portions of the bone screws can be threaded into the vertebrae to a desired depth and/or desired orientation relative to the orthopedic implants, such as implants 20 and/or 320. In many instances of spinal surgery, a surgeon will orient elongate implants, such as implants 20 and/or 320, so that the implants are positioned substantially parallel to a portion of the spine. In certain embodiments, once any and all adjustments are made to reach the proper and desired positioning of the selected orthopedic implant, the orthopedic implant can be locked in the desired position.

In certain embodiments, an orthopedic disc implant, such as implant 120 as an example, can be implanted according to known procedures between adjacent vertebrae in the intervertebral disc space. Such an orthopedic implant may at least partially replace a removed intervertebral disc, and may mimic the function of the intervertebral disc. In other embodiments, an orthopedic spacer implant, such as implant 220 as an example, can be implanted according to known procedures between spinous processes of adjacent vertebrae to provide an interspinous spacer implant to the spinal segment of the patient.

According to the present disclosure, methods of providing in vivo performance measurements of the orthopedic implants described above involve use and positioning analysis of radiopaque markers 28 discussed herein with respect to each other. As described above, an implant used in accordance with the present disclosure includes a set of radiopaque markers, such as markers 28, integrated or affixed therewith, capable of providing a visual representation upon application of a medical imaging technique. The markers are positioned on or in the movable portion of the implant at known positions and in a first known and predetermined relationship to each other. In certain embodiments, three radiopaque markers 28 are placed at positions which are movable with respect to each other. Additionally, it is contemplated that the markers can be integrated into the implant in the manners described above either before or after implantation of the implant into the patient's body.

A medical imaging technique can be applied to the orthopedic implant having a set of radiopaque markers, such as implant 20, 120, 220 or 320, which provides at least one image of the markers according to a second changed relationship resulting from movement of the orthopedic implant. In certain embodiments, the movement or force experienced by the implant, and the magnitude thereof, corresponds to compression, distraction, flexion, extension and/or rotation of the corresponding spinal segment as described above in connection with FIGS. 7A-7E. Additionally in certain embodiments, the medical imaging techniques which can be used in connection with the present disclosure can be radiation-based techniques, such as computed tomography scans (or CT scans), fluoroscopic techniques, electromagnetic radiation techniques, radio communication techniques, X-ray radiation or other such appropriate radiograph techniques. Additionally in certain embodiments, magnetic resonance imaging (MRI) or other techniques can be used. Additionally, it is contemplated that the medical imaging technique can be applied from any appropriate direction or location, such as anterior, posterior, or lateral locations relative to the spinal segment of the patient. It has been found that relative positions of markers can be determined spatially, in three dimensions, using time-of-flight calculations from electromagnetic (E/M) or radio frequency (RF) signals originating from one or more sources outside the body. This imaging is interpretive in nature, since the calculations determine the spatial relationship of the markers and thus they can be visualized as object in three dimensions. Thus, a visible image (e.g. x-ray) can be used, or such interpretive imaging can be used to create an image or diagram.

The image(s) received as a result of application of a medical imaging technique illustrate radiopaque markers 28 in changed relationships from the first known and predetermined relationship, i.e. a neutral relationship or one provided through manufacture. The changes in relative positions and relationships of radiopaque markers 28 can correspond to operating loads, moments or stresses imparted on the orthopedic implant according to various mathematical relationships. Accordingly, from the first known and predetermined relationship and the changed relationships, indications of performance of the orthopedic implant can be measured. As an example, a user of the system can determine the operating load of the implant based on the first and second relationships of the radiopaque markers.

From the operating load, various other indications of performance can optionally be determined. As an example, a user of the system can determine the load sharing occurring between the orthopedic implant under analysis and one or more other orthopedic implant devices implanted in the patient. In certain embodiments, the operating load impacting the orthopedic implant during particular events can be determined from evaluating the changed relationships of the markers corresponding to compression, distraction, flexion, extension and/or rotation experienced by the orthopedic implant, motions described above in connection with FIGS. 7A-7E. Additionally, a user of the system can evaluate the overall success or failure of the orthopedic implant and, in certain embodiments, can predict or anticipate an expected failure of the orthopedic implant.

In certain embodiments, multiple applications of a medical imaging technique can be performed, thereby allowing a user of the system to determine the operating load of the orthopedic implant at multiple moments in time and/or positions of the implant via the changed relationships of radiopaque markers 28. Substantially simultaneously with the applications of the medical imaging techniques, various other parameters can be measured. In such embodiments, a user of the system can correlate the operating load experienced by the orthopedic implant with the other measured parameters. As examples, correlated parameters can include pain, muscle activation, vertebral spacing, vertebral angle and percent range of motion, as well as pressure or other such forces impacting the orthopedic implant.

Additionally in certain embodiments, a user of the system can measure the bend angle of the orthopedic implant resulting from flexion or extension of the spinal segment. Referring to FIG. 7C as an example, the angle of bend of orthopedic implant 20 can be determined by measuring the segment distances between superior marker 50 and center marker 51, and center marker 51 and inferior marker 52. The distances are then used in accordance with the law of cosines to determine the bend angle orthopedic implant 20 is experiencing.

It should be appreciated that other forces, loads, moments and/or stresses experienced by the orthopedic implant, as well as overall in-vivo performance, may be determined according to the present disclosure. Additionally, it should be appreciated that other indications of performance of the device may be measured. Further, information regarding the implanted or adjacent tissues (e.g. breakdown or injury) may become apparent from the comparison of the positioning or other characteristics of radiopaque markers 28 at different times. In response to the indications of performance of the implant, the user of the system, typically a medical professional, can alter properties of the orthopedic implant and/or mandate certain recovery activities for the patient, or proceed otherwise as desired and/or deemed necessary by the user.

The various portions and components of orthopedic implants 20, 120, 220 and 320 can generally be composed of biocompatible materials that allow for the performance of the implants and methods as described herein, and that are also compatible with devices with which the orthopedic implants will be used. It will be appreciated that materials other than those described above could also be used.

While the disclosure has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method, comprising:
providing an orthopedic implant device having at least one movable portion, wherein said device includes at least two radiopaque markers integrated with said device in a first known, predetermined relationship;
implanting said device adjacent at least one vertebra of a spinal segment of a patient;
applying a medical imaging technique to said device at a first moment in time, wherein said applying provides at least one image of said markers in a second, changed relationship resulting from movement of said implant;
evaluating the relative positions of said markers in said second, changed relationship;
measuring at least one indication of performance of said device based at least on said second, changed relationship; and
determining the expected life span of said implant device based on said indication of performance.

2. The method of claim 1, wherein said measuring includes measuring the bending and rotation of said implant device.

3. The method of claim 1, comprising changing at least one property of said implant device based on said measured indication of performance.

4. The method of claim 1, comprising mandating at least one recovery activity for the patient based on said measured indication of performance.

5. The method of claim 1, comprising:
applying said medical imaging technique to said implant device at a second moment in time, wherein said applying provides at least one image of said markers in a third, changed relationship resulting from movement of said implant device;
evaluating the relative positions of said markers in said third, changed relationship; and
measuring at least one indication of performance of said implant device based at least on said third, changed relationship.

6. The method of claim 5, wherein the first moment in time corresponds to a first position of the spinal segment and the second moment in time corresponds to a second position of the spinal segment.

7. The method of claim 5, comprising correlating each of said relationships with at least one physical parameter of the patient.

8. The method of claim 7, wherein said at least one physical parameter is selected from the group consisting of pain, muscle activation, and vertebral spacing.

9. A method, comprising:
providing an orthopedic implant device having at least one movable portion, wherein said device includes at least two radiopaque markers integrated with said device in a first known, predetermined relationship;
implanting said device adjacent at least one vertebra of a spinal segment of a patient;
applying a medical imaging technique to said device at a first moment in time, wherein said applying provides at least one image of said markers in a second, changed relationship resulting from movement of said implant;
evaluating the relative positions of said markers in said second, changed relationship;
measuring at least one indication of performance of said device based at least on said second, changed relationship; and
predicting the expected time until failure of said implant device based on said indication of performance.

10. The method of claim 9, wherein said measuring includes measuring the bending and rotation of said implant device.

11. The method of claim 9, comprising changing at least one property of said implant device based on said measured indication of performance.

12. The method of claim 9, comprising mandating at least one recovery activity for the patient based on said measured indication of performance.

13. The method of claim 9, comprising:
applying said medical imaging technique to said implant device at a second moment in time, wherein said applying provides at least one image of said markers in a third, changed relationship resulting from movement of said implant device;
evaluating the relative positions of said markers in said third, changed relationship; and
measuring at least one indication of performance of said implant device based at least on said third, changed relationship.

14. The method of claim 13, wherein the first moment in time corresponds to a first position of the spinal segment and the second moment in time corresponds to a second position of the spinal segment.

15. The method of claim 13, comprising correlating each of said relationships with at least one physical parameter of the patient.

16. The method of claim 15, wherein said at least one physical parameter is selected from the group consisting of pain, muscle activation, and vertebral spacing.

17. A method, comprising:
providing an orthopedic implant device having at least one movable portion, wherein said device includes at least two radiopaque markers integrated with said device in a first known, predetermined relationship;
implanting said device adjacent at least one vertebra of a spinal segment of a patient;
applying a medical imaging technique to said device at a first moment in time, wherein said applying provides at least one image of said markers in a second, changed relationship resulting from movement of said implant;
evaluating the relative positions of said markers in said second, changed relationship;
measuring at least one indication of performance of said device based at least on said second, changed relationship; and
determining the load-sharing relationship between said implant device and at least one other orthopedic device implanted adjacent the spinal segment of the patient, wherein said at least one indication of performance is the operating load of said implant device.

18. The method of claim 17, wherein said measuring includes measuring the bending and rotation of said implant device.

19. The method of claim 17, comprising changing at least one property of said implant device based on said measured indication of performance.

20. The method of claim 17, comprising mandating at least one recovery activity for the patient based on said measured indication of performance.

21. The method of claim 17, comprising:
applying said medical imaging technique to said implant device at a second moment in time, wherein said applying provides at least one image of said markers in a third, changed relationship resulting from movement of said implant device;

evaluating the relative positions of said markers in said third, changed relationship; and measuring at least one indication of performance of said implant device based at least on said third, changed relationship.

22. The method of claim 21, wherein the first moment in time corresponds to a first position of the spinal segment and the second moment in time corresponds to a second position of the spinal segment.

23. The method of claim 21, comprising correlating each of said relationships with at least one physical parameter of the patient.

24. The method of claim 23, wherein said at least one physical parameter is selected from the group consisting of pain, muscle activation, and vertebral spacing.

* * * * *